US010449529B2

(12) United States Patent
Balaraman et al.

(10) Patent No.: US 10,449,529 B2
(45) Date of Patent: Oct. 22, 2019

(54) PHENANTHROLINE BASED PINCER COMPLEXES USEFUL AS CATALYSTS FOR THE PREPARATION OF METHANOL FROM CARBONDIOXIDE

(71) Applicant: Council of Scientific and Industrial Research, New Delhi, Delhi (IN)

(72) Inventors: Ekambaram Balaraman, Maharashtra (IN); Vinod Gokulkrishna Landge, Maharashtra (IN); Siba Prasad Midya, Maharashtra (IN); Manoj Kumar Sahoo, Maharashtra (IN); Garima Jaiswal, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/549,827

(22) PCT Filed: Feb. 10, 2016

(86) PCT No.: PCT/IN2016/050050
§ 371 (c)(1),
(2) Date: Aug. 9, 2017

(87) PCT Pub. No.: WO2016/128997
PCT Pub. Date: Aug. 18, 2016

(65) Prior Publication Data
US 2018/0021766 A1 Jan. 25, 2018

(30) Foreign Application Priority Data

Feb. 10, 2015 (IN) .............................. 358/DEL/2015
Feb. 13, 2015 (IN) .............................. 417/DEL/2015

(51) Int. Cl.
*B01J 31/00* (2006.01)
*B01J 31/18* (2006.01)
*B01J 31/20* (2006.01)
*B01J 31/24* (2006.01)
*C07F 15/00* (2006.01)

(52) U.S. Cl.
CPC ........... *B01J 31/189* (2013.01); *B01J 31/183* (2013.01); *B01J 31/1815* (2013.01); *B01J 31/20* (2013.01); *B01J 31/2404* (2013.01); *B01J 31/2447* (2013.01); *C07F 15/0046* (2013.01); *B01J 2231/643* (2013.01); *B01J 2231/648* (2013.01); *B01J 2231/763* (2013.01); *B01J 2531/0244* (2013.01); *B01J 2531/821* (2013.01)

(58) Field of Classification Search
None
See application file for complete search history.

(56) References Cited

U.S. PATENT DOCUMENTS

2009/0112005 A1 4/2009 Milstein et al.
2013/0281664 A1 10/2013 Milstein et al.

FOREIGN PATENT DOCUMENTS

| CN | 103980317 A | 8/2014 |
| WO | 2006/106484 A1 | 10/2006 |
| WO | 2012/052996 A2 | 4/2012 |
| WO | 2012/052996 A3 | 4/2012 |

OTHER PUBLICATIONS

Balaraman et al. (JACS, 132, 16756-16758 (Year: 2010).*
Adriana Valore et al., "Novel ruthenium(II) complexes with substituted 1,10-phenanthroline or 4,5-diazafluorene linked to a fullerene as highly active second order NLO chromophores" published in Dalton Trans., 2010,39, 10314-10318.
Langer et al., "Stepwise Metal—Ligand Cooperation by a Reversible Aromatization/Deconjugation Sequence in Ruthenium Complexes with a Tetradentate Phenanthroline-Based Ligand" published in Chemistry, 2013;19(10), pp. 3407-3414.
J Zhang et al., "Electron-Rich PNP- and PNN-Type Ruthenium (II) Hydrido Borohydride Pincer Complexes. Synthesis, Structure, and Catalytic Dehydrogenation of Alcohols and Hydrogenation of Esters" published in Organometallics, 2011, 30 (21), pp. 5716-5724.
Rigoberto Barrios-Francisco et al., "PNN Ruthenium Pincer Complexes Based on Phosphinated 2,2'-Dipyridinemethane and 2,2'-Oxobispyridine. Metal—Ligand Cooperation in Cyclometalation and Catalysis" published in Organometallics, 2013, 32 (10), pp. 2973-2982.
Boopathy Gnanaprakasam et al., "Synthesis of Amides from Esters and Amines with Liberation of H2 under Neutral Conditions" published in J. Am. Chem. Soc., 2011, 133 (6), pp. 1682-1685.
Jing Zhang et al., "Facile Conversion of Alcohols into Esters and Dihydrogen Catalyzed by New Ruthenium Complexes" published in in J. am. chem. soc., 2005, 127, 10840-10841.
Yu-Nong Li et al, "Homogeneous hydrogenation of carbon dioxide to methanol" published in Catalysis Science & Technology, 2014, 4(6), pp. 1498-1512.
Sebastian Wesselbaum et al., "Hydrogenation of carbon dioxide to methanol using a homogeneous ruthenium-Triphos catalyst: from mechanistic investigations to multiphase catalysis" published in Chemical Science, 2015, 6, 693-704.
Sebastian Wesselbaum et al., "Hydrogenation of carbon dioxide to methanol by using a homogeneous ruthenium-phosphine catalyst" published in Angewandte Chemie International Edition, 2012, 51(30):7499-7502.
Chelsea Ariane Huff, "Cascade catalysis for the homogeneous hydrogenation of carbon dioxide to methanol" published in Journal of the American Chemical Society, 2011, 133, 18122-18125.

(Continued)

*Primary Examiner* — Yun Qian
(74) *Attorney, Agent, or Firm* — Katten Muchin Rosenman LLP

(57) ABSTRACT

The present invention relates to a novel phenonthroline based pincer complexes and process for preparation thereof. The present invention also provides a one pot process for the conversion of carbon dioxide to methanol in the presence of a molecularly defined pincer-type single-site Ru-catalyst and secondary amine. Further the present invention provides the use of phenonthroline based pincer complexes for the esterification of alcohols and hydrogenation of esters under mild conditions.

5 Claims, 1 Drawing Sheet

(56) References Cited

OTHER PUBLICATIONS

Dr. Ekambaram Balaraman et al., "Unprecedented catalytic hydrogenation of urea derivatives to amines and methanol", published in Angewandte Chemie International Edition, 2011, 50(49):11702-11705.
Jotheeswari Kothandaraman et al., "Conversion of CO2 from air into methanol using a polyamine and a homogeneous ruthenium catalyst", published in Journal of American Chemical Society, 2015, pp. 778-781.
Huang F et al., "How does the nickel pincer complex catalyze the conversion of CO2 to a methanol derivative? A computational mechanistic study", published in Inorganic Chemistry, 2011, 18;50(8), pp. 3816-3825.
Ekambram Balaraman, "Efficient hydrogenation of organic carbonates, carbamates and formates indicates alternative routes to methanol based on CO2 and CO", published in Nature Chemistry, vol. 3, Aug. 2011, www.nature.com/naturechemistry, pp. 609-614.
Pierre H. Dixneuf, "A bridge from CO2 to methanol", Nature Chemistry, vol. 3, Aug. 2011, www.nature.com/naturechemistry, pp. 578-579.
International Search Report and Written Opinion dated Jul. 12, 2016, from the corresponding PCT/IN2016/050050.
International International Preliminary Report on Patentability dated Mar. 21, 2017, from the corresponding PCT/IN2016/050050.
Pierre H. Dixneuf, "Bifunctional catalysis: A bridge from CO2 to methanol" published in Nature Chemistry, Nature Publishing Group, GB, vol. 3, Aug. 1, 2011, pp. 578-579, XP009150767, ISSN: 1755-4330, figure 1, the whole document.
Chelsea A. Huff et al., "Cascade catalysis for the homogeneous hydrogenation of CO2 to methanol", published in Journal of American Chemical Society, vol. 133, No. 45, Oct. 26, 2011, pp. 18122-18125, XP055023110, ISSN: 0002-7863, D01: 10.1021/ja208760j Scheme 2; table 1; compounds C-1, C-2.
Balaraman, E, et al., "Efficient hydrogenation of organic carbonates, carbamates and formates indicates alternative routes to methanol based on CO2 and CO" published in Nature Chemistry, 2011, vol., No. 8, Jan. 1, 2011, pp. 609-614, XP009150768, ISSN: 1755-4330, figures 1, 4; compounds 1-4, abstract.

\* cited by examiner

PHENANTHROLINE BASED PINCER COMPLEXES USEFUL AS CATALYSTS FOR THE PREPARATION OF METHANOL FROM CARBONDIOXIDE

FIELD OF THE INVENTION

The present invention relates to phenonthroline based pincer complex of formula (I) and process for preparation thereof. Particularly the present invention relates to use of phenonthroline based pincer complex of formula (I) as catalyst for the esterification of alcohols and hydrogenation of esters including lactones under mild conditions. More particularly the present invention relates to a one pot process for the conversion of carbon dioxide to methanol in the presence of a pincer based catalyst and a secondary amine wherein the secondary amine is recovered and recycled.

BACKGROUND OF THE INVENTION

In the state-of-the-art catalysis, design and development of new catalytic systems for selective organic transformations is of significant interest, though very challenging. Particularly, alternative 'green' approaches to traditionally employing stoichiometric reagents and/or harsh conditions in industrially important reactions are extremely essential with regard to both energy and environment. The direct conversion of alcohols to value-added products and hydrogenation of carbonyl compounds to the corresponding alcohols and/or amines are benchmark reactions. Alcohol esterification is one of the most important reactions in synthetic organic chemistry and has potential applications including in fragrance, polymer, and pharmaceutical industries. The reaction is typically carried-out by coupling of activated carboxylic acid derivatives with an alcohol and produce stoichiometric acid waste. An ideal and alternative approach would be catalytic acceptorless dehydrogenation of alcohols with the evolution of molecular hydrogen, but homogeneous systems capable of catalyzing dehydrogenation of alcohols are relatively rare.

Catalytic hydrogenation of carboxylic acid derivatives, particularly esters with hydrogen gas, provides a promising alternative approach to conventional reduction methods. The operational simplicity, 'green' approach and economic viability are additional advantages and make this method much more attractive. In industry, this process is carried out under heterogeneous conditions using catalysts such as copper chromite at high pressure (200-300 atm) and temperatures (200-300° C.).

Article titled "Novel ruthenium(II) complexes with substituted 1,10-phenanthroline or 4,5-diazafluorene linked to a fullerene as highly active second order NLO chromophores" by Adriana Valore et al. published in *Dalton Trans.*, 2010, 39, 10314-10318 reports Ru(II) complexes with substituted 1,10-phenanthroline or 4,5-diazafluorene.

Article titled "Stepwise Metal-Ligand Cooperation by a Reversible Aromatization/Deconjugation Sequence in Ruthenium Complexes with a Tetradentate Phenanthroline-Based Ligand" by Langer et al. published in *Chemistry*, 2013; 19(10), pp 3407-14 reports synthesis and reactivity of ruthenium complexes containing the tetradentate phenanthroline-based phosphine ligand 2,9-bis((di-tert-butylphosphino)methyl)-1,10-phenanthroline (PPhenP).

Chinese patent application no. 103980317 discloses a dipyridyl tetradentate ligand ruthenium complex as well as a preparation method of the complex and application of the complex to a reaction for hydrogenating ester compounds into alcohol compounds.

US patent application no. 20130281664 discloses novel ruthenium catalysts and related borohydride complexes, and the use of such catalysts for (1) hydrogenation of amides (including polyamides) to alcohols and amines; (2) preparing amides from alcohols with amines (including the preparation of polyamides (e.g., polypeptides) by reacting dialcohols and diamines and/or by polymerization of amino alcohols); (3) hydrogenation of esters to alcohols (including hydrogenation of cyclic esters (lactones) or cyclic di-esters (di-lactones) or polyesters); (4) hydrogenation of organic carbonates (including polycarbonates) to alcohols and hydrogenation of carbamates (including polycarbamates) or urea derivatives to alcohols and amines; (5) dehydrogenative coupling of alcohols to esters; (6) hydrogenation of secondary alcohols to ketones.

Article titled "Electron-Rich PNP- and PNN-Type Ruthenium (II) Hydrido Borohydride Pincer Complexes. Synthesis, Structure, and Catalytic Dehydrogenation of Alcohols and Hydrogenation of Esters" By J Zhang et al. published in *Organometallics*, 2011, 30 (21), pp 5716-5724 reports Electron-rich PNP- and PNN-type ruthenium(II) hydrido borohydride pincer complexes, [RuH(BH$_4$)(tBu-PNP)] (tBu-PNP=(2,6-bis(di-tert-butylphosphinomethyl)pyridine) (5) and [RuH(BH$_4$)(tBu-PNN)] (tBu-PNN=2-di-tert-butylphosphinomethyl-6-diethylaminomethylpyridine) (6), prepared from their corresponding N$_2$-bridged dinuclear Ru(II) complexes [(tBu-PNP)RuCl$_2$]2(μ-N$_2$) (3) and [(tBu-PNN)RuCl$_2$]2(μ-N$_2$) (4), respectively.

Article titled "PNN Ruthenium Pincer Complexes Based on Phosphinated 2,2'-Dipyridinemethane and 2,2'-Oxobispyridine. Metal-Ligand Cooperation in Cyclometalation and Catalysis" By Rigoberto Barrios-Francisco et al. published in *Organometallics*, 2013, 32 (10), pp 2973-2982 reports synthesis of novel PNN ruthenium pincer complexes based on 2,2'-dipyridinemethane phosphine derivatives, as well as on 2,2'-oxobispyridine phosphine ligands, and their reactivity toward dearomatization and cyclometalation.

Article titled "Synthesis of Amides from Esters and Amines with Liberation of H$_2$ under Neutral Conditions" by Boopathy Gnanaprakasam et al. published in *J. Am. Chem. Soc.*, 2011, 133 (6), pp 1682-1685 reports efficient synthesis of amides directly from esters and amines is achieved under mild, neutral conditions with the liberation of molecular hydrogen which is homogeneously catalyzed under neutral conditions by a dearomatized Ru-pincer PNN complex.

PCT application No. 2006106484A1 discloses catalytic hydrogenation and use of Ru complexes with tetradentate ligands, having at least one amino or imino coordinating group and at least one phosphino coordinating group, in hydrogenation processes for the reduction of esters or lactones into the corresponding alcohol or diol respectively.

Article titled "Facile Conversion of Alcohols into Esters and Dihydrogen Catalyzed by New Ruthenium Complexes" by Jing Zhang et al. published in in *J. am. chem. soc.*, 2005, 127, 10840-10841 reports Ru(II) hydride complexes based on electron rich PNP and PNN ligands catalyze alcohol dehydrogenation to esters.

Heterogeneous catalytic systems for direct hydrogenation of CO$_2$ to methanol require high temperature and pressure and often selectivity is the major issue. Owing to rational tuning of reactivity and selectivity of homogeneous catalysts much attention has been paid for their utility in selective hydrogenation of CO$_2$. In recent years, pincer ligands which bind to metal centers in a tri-dentate, meridional fashion have drawn much attention and serve as excellent ligands, due to stability and variability of the generated metal-ligand framework. The donor/acceptor ability at both the central and adjacent side-arm positions of the pincer ligands can be controllable. And both the electronic and steric environment around the metal center can also be tunable.

Article titled "Carbon dioxide hydrogenation to methanol at low pressure and temperature" by Bill Alain published in EPFL, 1998 reports the conversion of $CO_2$ with hydrogen to methanol is investigated in dielectric-barrier discharges with and without catalysts at low temperatures ($\leq 100°$ C.) and pressures ($\leq 10$ bar).

Article titled "Bifunctional catalysis: A bridge from $CO_2$ to methanol" by Pierre H. Dixneuf published in Nature Chemistry, 2011, 3, pp 578-579 reports methanol can be produced via the hydrogenation of carbonates and carbamates using a pincer ruthenium(II) catalyst.

Article titled "Homogeneous hydrogenation of carbon dioxide to methanol" by Yu-Nong Li et al. published in Catalysis Science & Technology, 2014, 4(6), pp 1498-1512 reports metal complexes and organocatalysts for $CO_2$ hydrogenation to methanol have been developed along with the reaction mechanistic insight. Understanding the interaction of active catalytic species with $CO_2$ or hydrogen could account for development of efficient homogeneous catalysts.

Article titled "Hydrogenation of carbon dioxide to methanol using a homogeneous ruthenium-Triphos catalyst: from mechanistic investigations to multiphase catalysis" by Sebastian Wesselbaum et al. published in Chemical Science, 2015, 6, 693-704 reports Hydrogenation of carbon dioxide to methanol using a homogeneous ruthenium-Triphos catalyst: from mechanistic investigations to multiphase catalysis.

Article titled "Hydrogenation of carbon dioxide to methanol by using a homogeneous ruthenium-phosphine catalyst" by Sebastian Wesselbaum et al. published in Angewandte Chemie International Edition, 2012, 51(30):7499-502 reports the homogenously catalyzed hydrogenation of $CO_2$ to methanol is achieved by using a ruthenium phosphine complex under relatively mild conditions (HNTf2=bis(trifluoromethane)sulfonimide). This is the first example of $CO_2$ hydrogenation to methanol by using a single molecularly defined catalyst.

Article titled "Cascade hydrogenation of carbon dioxide to methanol" by Chelsea Ariane Huff published as thesis in 2014 reports use of homogeneous catalysts in tandem for the hydrogenation of $CO_2$ to $CH_3OH$ at relatively high temperature ($135°$ C.).

Article titled "Tandem amine and ruthenium-catalyzed hydrogenation of $CO_2$ to methanol" by Rezayee N M et al. published in Journal of American Chemical Society, 2015, 28; 137(3), pp 1028-31 reports the hydrogenation of carbon dioxide to methanol via tandem catalysis with dimethylamine and a homogeneous ruthenium complex. The dimethylamine is proposed to play a dual role in this system. It reacts directly with $CO_2$ to produce dimethylammonium dimethylcarbamate, and it also intercepts the intermediate formic acid to generate dimethylformamide. With the appropriate selection of catalyst and reaction conditions, >95% conversion of $CO_2$ was achieved to form a mixture of $CH_3OH$ and dimethylformamide.

Article titled "Examining ruthenium chromophores for the photochemical reduction of $CO_2$ to methanol" by David J Boston published as thesis in 2013 reports photochemical reduction of carbon dioxide to methanol is possible using pyridine and the complex $[Ru(phen)_2dppz](PF_6)_2$, $[Ru(phen)_2pbtp\alpha](PF_6)_2$, and $[Ru(phen)_2pbtp\beta](PF_6)_2$.

Article titled "Cascade catalysis for the homogeneous hydrogenation of $CO_2$ to methanol" by Chelsea A. Huff et al. published in Journal of American Chemical Society, 2011, 133 (45), pp 18122-18125 reports the homogeneous hydrogenation of $CO_2$ to CH3OH via cascade catalysis. Three different homogeneous catalysts, $(PMe3)_4Ru(Cl)(OAc)$, $Sc(OTf)_3$, and $(PNN)Ru(CO)(H)$, operate in sequence to promote this transformation.

Article titled "Efficient hydrogenation of organic carbonates, carbamates and formates indicates alternative routes to methanol based on $CO_2$ and CO" by Balaraman E et al. published in Nature Chemistry, 2011, 3(8), pp 609-14 reports catalytic hydrogenation of organic carbonates to alcohols, and carbamates to alcohols and amines. Unprecedented homogeneously catalysed hydrogenation of organic formates to methanol has also been accomplished. The reactions are efficiently catalysed by dearomatized PNN Ru(II) pincer complexes derived from pyridine- and bipyridine-based tridentate ligands.

Article titled "Unprecedented catalytic hydrogenation of urea derivatives to amines and methanol" by Dr. Ekambaram Balaraman et al. published in Angewandte Chemie International Edition, 2011, 50(49):11702-11705 reports hydrogenation of urea derivatives to the corresponding amines and methanol is reported. The reaction is catalyzed by a bipyridine-based tridentate PNN Ru(II) pincer complex and proceeds under mild, neutral conditions using 13.6 atm of $H_2$. A mild approach is offered for the indirect hydrogenation of $CO_2$ to methanol as urea derivatives are available from $CO_2$.

Article titled "Conversion of $CO_2$ from air into methanol using a polyamine and a homogeneous ruthenium catalyst" by Jotheeswari Kothandaraman et al. published in Journal of American Chemical Society, 2015 reports a highly efficient homogeneous catalyst system for the production of $CH_3OH$ from $CO_2$ using pentaethylenehexamine and Ru-Macho-BH (1) at 125-165° C. in an ethereal solvent has been developed (initial turnover frequency=70 $h^{-1}$ at 145° C.).

Article titled "How does the nickel pincer complex catalyze the conversion of $CO_2$ to a methanol derivative? A computational mechanistic study" by Huang F et al. published in *Inorganic Chemistry*, 2011, 18; 50(8), pp 3816-25 reports the mechanistic details of nickel-catalyzed reduction of $CO_2$ with catecholborane (HBcat) have been studied only by DFT calculations. The nickel pincer hydride complex $(\{2,6\text{-}C_6H_3(OP(t)Bu_2)_2\}NiH=[Ni]H)$ has been shown to catalyze the sequential reduction from $CO_2$ to HCOOBcat, then to $CH_2O$, and finally to $CH_3OBcat$.

However, there is a need in the art to develop novel catalyst for an atom-economical, environmentally benign and operationally simple synthetic process from the feedstock chemicals for the direct conversion of alcohols to esters and efficient hydrogenation of esters to alcohols under solvent-free reaction conditions.

OBJECTIVE OF THE INVENTION

The main objective of the present invention is to provide a phenanthroline based pincer complex of formula (I).

Another objective of the present invention is to provide a process for the synthesis of novel phenanthroline based pincer complex of formula (I).

Still another objective of the present invention is to provide a process for the hydrogenation and dehydrogenation reactions using phenanthroline based pincer complex of formula (I) as catalyst.

Still another objective of the present invention is to provide a one pot process for the conversion of carbon dioxide to methanol in the presence of a pincer based catalyst and a secondary amine under mild conditions with improved yield.

SUMMARY OF THE INVENTION

Accordingly the present invention provides a phenanthroline based pincer catalyst complexes of Formula (I);

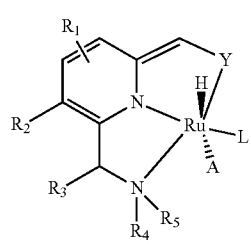

Formula (I)

wherein

M is a noble metal, transition metal ($1^{st}$, $2^{nd}$ and $3^{rd}$ row of elements), alkaline-earth—or rare-earth elements;

Y is selected from the group consisting of phosphine ($PR^aR^b$), phosphite $P(OR^a)(OR^b)$, phosphinite $P(OR^a)(R^b)$, amine ($NR^aR^b$), imine, sulphide $SR^a$, oxide $OR^a$, sulfoxide $S(O)R^a$, sulphone $SO_2R^a$, oxazoline, N-heterocyclic carbine, heteroaryl containing at least one heteroatom selected from nitrogen or Sulphur;

L is selected from the group consisting of CO, $BH_3$, $BH_2$, $PR^aR^bR^c$, $P(OR^a)(OR^b)(OR^c)$, nitrile (RCN) or isonitrile (RNC);

R, $R^a$, $R^b$, and $R^c$ are selected from the group consisting of alkyl, cycloalkyl, aryl which may be further substituted heterocyclyl, heteroaryl, alkylcycloalkyl, alkylaryl, alkylheterocyclyl, alkylheteroaryl.

A ligand used is aromatic or dearomatic is selected from the group consisting of H, halogen, OCOR, $OCOCF_3$, $OSO_2R$, $OSO_2CF_3$, CN, OR, $N(R)_2$ and RS;

$R^1$, represents hydrogen or one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—$CO_2R$), —OC(O)R, —$OC(O)CF_3$, —$OSO_2R$, —$OSO_2CF_3$) cyano, alkoxy, alkylamino (mono or di), arylamino (mono or di), —SR, an inorganic support or a polymeric moiety.

$R^2$ and $R^3$ form a 6 membered aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—$CO_2R$), —OC(O)R, —$OC(O)CF_3$, —$OSO_2R$, —$OSO_2CF_3$) cyano, alkoxy, alkylamino (mono or di), arylamino (mono or di), —SR, an inorganic support or a polymeric moiety.

$R^3$ and $R^4$ form a six member aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—$CO_2R$), —OC(O)R, —$OC(O)CF_3$, —$OSO_2R$, —$OSO_2CF_3$) cyano, alkoxy, alkylamino (mono or di), arylamino (mono or di), —SR, an inorganic support or a polymeric moiety.

In an embodiment present, invention provides a phenanthroline based pincer complexes of formula (I) as claimed in claim 1, wherein said complex is selected from HCl(CO)Ru(Phen-(tBu)PNN) (3), H(CO)Ru-(Phen-(tBu)PNN) (4) and H(CO)Ru(η1BH4)(Phen-(tBu)PNN) (5a).

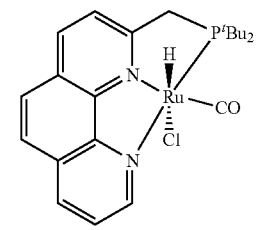

3

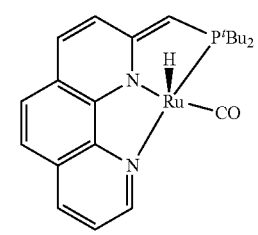

4

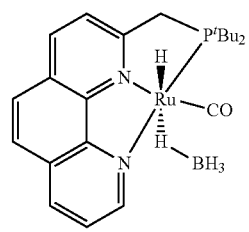

5a

In another embodiment of present invention, the said catalyst is used for hydrogenation of lactones to diols and esters to alcohols In still another embodiment of present invention, the said catalyst is used for dehydrogenation of diols to lactones, alcohol to esters and secondary alcohols to ketones.

In yet another embodiment, present invention provides a process for the preparation of phenanthroline based pincer complexes of formula (I) as claimed in claim 1, wherein said process comprising the steps of:

a) adding solution of Lithium diisopropylamide and tBuOK in suitable solvent to a solution of 2-methyl-1, 10-phenanthroline (1) in ether at a temperature in the range of 0 to 5° C. followed by stirring the reaction mixture for the period in the range of 30 to 40 min to obtain a solution;

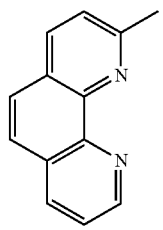

(1)

b) adding a solution of di-tert-butylchlorophosphine in ether to the solution as obtained in step (a) and stirring for a period of 1 to 2 hr at a temperature in the range of −50 to −78° C. followed by stirring at temperature in the range of 25 to 30° C. for the period in the range of 12 to 14 hrs to obtain Phen-PNN($^t$Bu) (2);

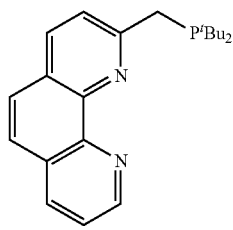

(2)

c) mixing the Phen-PNN(tBu) (2) as obtained in step (b), RuHCl(CO)(PPh$_3$)$_3$ and tetrahydrofuran heating at a temperature in the range of 60 to 70° C. for the period in the range of 5 to 6 hr under argon atmosphere to obtain HCl(CO)Ru(Phen-($^t$Bu)PNN) (3);

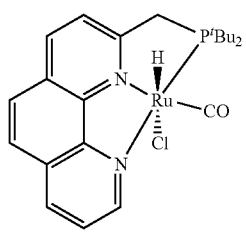

(3)

d) adding Sodium bis(trimethylsilyl)amide to the compound of step (c) in C$_6$H$_6$ to obtain H(CO)Ru-(Phen-($^t$Bu)PNN) (4);

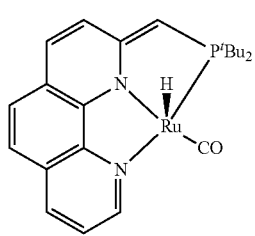

(4)

e) stirring the reaction mixture comprising HCl(CO)Ru(Phen-(tBu)PNN) (3) and NaBH$_4$ in toluene and ethanol at temperature in the range of 50 to 70° C. for the period in the range of 10 to 15 min followed by stirring at a temperature in the range of 25-30° C. for the period in the range of 4 to 6 hrs to obtain H(CO)Ru(η1BH4)(Phen-(tBu)PNN) (5a).

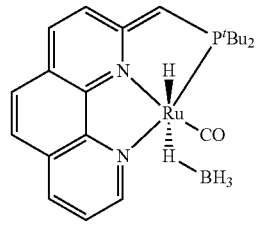

5a

In yet another embodiment of present invention, the solvent used in step (a) is selected from hexane, heptane, tetrahydrofuran (THF), diethyl ether, toluene, and etheylbenzene.

In yet another embodiment of present invention, the phenanthroline based pincer complexes of Formula (I) is useful for the preparation of methanol from carbon dioxide

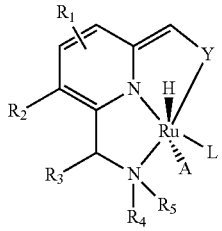

Formula (I)

wherein

M is a noble metal, transition metal (1$^{st}$, 2$^{nd}$ and 3$^{rd}$ row of elements), alkaline-earth—or rare-earth elements;

Y is selected from the group consisting of phosphine (PR$^a$R$^b$), phosphite P(OR$^a$)(OR$^b$), phosphinite P(OR$^a$)(R$^b$), amine (NR$^a$R$^b$), imine, sulphide SR$^a$, oxide OR$^a$, sulfoxide S(O)R$^a$, sulphone SO$_2$R$^a$, oxazoline, N-heterocyclic carbine, heteroaryl containing at least one heteroatom selected from nitrogen or Sulphur;

L is selected from the group consisting of CO, BH$_3$, BH$_2$, PR$^a$R$^b$R$^c$, P(OR$^a$)(OR$^b$)(OR$^c$), nitrile (RCN) or isonitrile (RNC);

R, R$^a$, R$^b$, and R$^c$ are selected from the group consisting of alkyl, cycloalkyl, aryl which may be further substituted heterocyclyl, heteroaryl, alkylcycloalkyl, alkylaryl, alkylheterocyclyl, alkylheteroaryl.

A ligand used is aromatic or dearomatic and is selected from the group consisting of H, halogen, OCOR, OCOCF$_3$, OSO$_2$R, OSO$_2$CF$_3$, CN, OR, N(R)$_2$ and RS;

R$^1$, represents hydrogen or one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, trifluromethyl, nitro, amide, ester (—CO$_2$R), —OC(O)R, —OC(O)CF$_3$, —OSO$_2$R, —OSO$_2$CF$_3$) cyano, alkoxy, alkylamino (mono or di), arylamino (mono or di), —SR, an inorganic support or a polymeric moiety.

$R^2$, $R^3$=H;

$R^2$ and $R^3$ form a 6 membered aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—$CO_2R$), —OC(O)R, —OC(O)$CF_3$, —$OSO_2R$, —$OSO_2CF_3$) cyano, alkoxy, alkylamino (mono or di), arylamino (mono or di), —SR, an inorganic support or a polymeric moiety;

$R^4$, $R^5$=H or $C_2H_5$;

$R^3$ and $R^4$ form a six member aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—$CO_2R$), —OC(O)R, —OC(O)$CF_3$, —$OSO_2R$, —$OSO_2CF_3$) cyano, alkoxy, alkylamino (mono or di), arylamino (mono or di), —SR, an inorganic support or a polymeric moiety.

wherein the said catalyst is useful for the preparation of methanol from carbon dioxide and the said process comprising the steps of:

i. mixing catalyst, secondary amine in a ratio of (1:500) in tetrahydrofuran to obtain a solution;
ii. adding potassium tert-butoxide (in case of catalysts 3 or 5 or 7 only) to the solution obtained in step (i) to obtain a solution;
iii. pressurizing the solution as obtained in step (ii) with carbon dioxide at 10 atmosphere followed by $H_2$ atmosphere at 30-40 atm to obtain a solution;
iv. heating the solution as obtained in step (iii) at 110-120° C. and stirring for 12-14 hrs to obtain a solution;
v. removing excess gases from the solution as obtained in step (iv) to obtain N-formylated product of secondary amine;
vi. adding catalyst and potassium tert-butoxide (in case of catalysts 3 or 5 or 7 only) to the N-formylated product of secondary amine as obtained in step (v) to obtain solution;
vii. pressurizing the solution as obtained in step (vi) with $H_2$ at 40-45 atmosphere followed by heating the solution at 110-120° C. and stirring for 18-20 hrs to obtain methanol and recyclable secondary amine.

In yet another embodiment of present invention, wherein catalyst of formula 1 used in step (i) is selected from HCl(CO)Ru(Phen-($^t$Bu)PNN) (3); H(CO)Ru-(Phen-($^t$Bu)PNN) (4); H(CO)Ru($\eta$1BH4)(Phen-(tBu)PNN) (5a); HCl(CO)Ru(BPy-$^t$PNN); [H(CO)Ru(BPy-$^t$PNN$^-$)]; and H(CO)Ru$^-$(Py-$^t$PNN)].

In yet another embodiment of present invention, wherein said steps (ii) and (vi) are absent when [H(CO)Ru(BPy-$^t$PNN)] catalyst is used.

In yet another embodiment of present invention, secondary amine used in step (i) is selected from A or B wherein;
X is selected from the group consisting of NH, $CH_2$, and O $R^1$ and $R^2$ are the same or different and is selected from the group consisting of alkyl (linear, branched), cyclo (up to 7 membered, which may be further mono, di, tri or tetra substituted and selected from the group consisting of alkyl (linear and branced), aryl (further substituted), cycloalkyl, alkylaryl, alkylheterocyclyl, alkylheteroaryl, halogen, triflurometyl, nitro, alkoxy, dialkylamino, diarylamino, and —SR), cycloalkyl, aryl (which may be further mono, di, tri or tetra substituted), heterocyclyl, heteroaryl, Abbreviations $CO_2$: Carbon dioxide
THF: Tetrahydro furan
$H_2$: Hydrogen
Phen-PNN(tBu): 2-((di-tert-butylphosphanyl)methyl)-1,10-phenanthroline
HCl(CO)Ru(Phen-(tBu)PNN): [2-((di-tert-butylphosphanyl)methyl)-1,10-phenanthroline] ruthenium(II) chlorocarbonyl hydride
H(CO)Ru-(Phen-(tBu)PNN): Carbonylhydrido[2-((di-tert-butylphosphanyl)methylene)-2H-1,10-phenanthrolin-1-ide]ruthenium(II)
HCl(CO)Ru(BPy-tPNN): [6-((di-tert-butylphosphanyl)methyl)-2,2'-bipyridine] ruthenium(II)chlorocarbonyl hydride
[H(CO)Ru-(BPy-tPNN-)]: Carbonylhydrido[6-((di-tert-butylphosphanyl)methylene)-6H-[2,2'-bipyridin]-1-ide]ruthenium(II)
HCl(CO)Ru(Py-tPNN-)]: [2-(Di-tert-butylphosphinomethyl)-6-(diethylaminomethyl) pyridine]ruthenium(II) chlorocarbonyl hydride

DETAILED DESCRIPTION OF THE INVENTION

Figure 1:
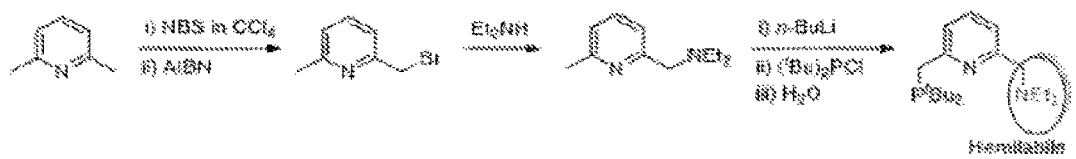
FIG. 1 depicts the schematic representation of synthesis of Milstein ligand.

The present invention provides novel phenanthroline based pincer complexes of formula (I) as shown below:

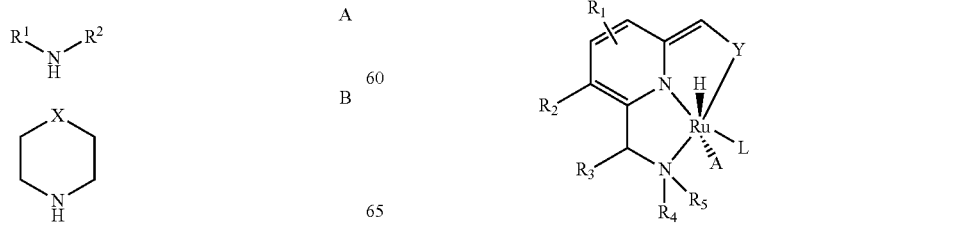

Formula (I)

wherein

M is a noble metal, transition metal (1$^{st}$, 2$^{nd}$ and 3$^{rd}$ row of elements), alkaline-earth—or rare-earth elements;

Y is selected from the group consisting of phosphine (PR$^a$R$^b$), phosphite P(OR$^a$)(OR$^b$), phosphinite P(OR$^a$)(R$^b$), amine (NR$^a$R$^b$), imine, sulphide SR$^a$, oxide OR$^a$, sulfoxide S(O)R$^a$, sulphone SO$_2$R$^a$, oxazoline, N-heterocyclic carbine, heteroaryl containing at least one heteroatom selected from nitrogen or Sulphur;

L is selected from the group consisting of CO, BH$_3$, BH$_2$, PR$^a$R$^b$R$^c$, P(OR$^a$)(OR$^b$)(OR$^c$), nitrile (RCN) or isonitrile (RNC);

R, R$^a$, R$^b$, and R$^c$ are selected from the group consisting of alkyl, cycloalkyl, aryl which may be further substituted heterocyclyl, heteroaryl, alkylcycloalkyl, alkylaryl, alkylheterocyclyl, alkylheteroaryl.

A ligand used is aromatic or dearomatic is selected from the group consisting of H, halogen, OCOR, OCOCF$_3$, OSO$_2$R, OSO$_2$CF$_3$, CN, OR, N(R)$_2$ and RS;

R$^1$, represents hydrogen or one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—CO$_2$R), —OC(O)R, —OC(O)CF$_3$, —OSO$_2$R, —OSO$_2$CF$_3$) cyano, alkoxy, alkylamino (mono or di), arylamino (mono or di), —SR, an inorganic support or a polymeric moiety.

R$^2$ and R$^3$ form a 6 membered aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—CO$_2$R), —OC(O)R, —OC(O)CF$_3$, —OSO$_2$R, —OSO$_2$CF$_3$) cyano, alkoxy, alkylamino (mono or di), arylamino (mono or di), —SR, an inorganic support or a polymeric moiety.

R$^3$ and R$^4$ form a six member aromatic ring which is further substituted with one or two substituents wherein each such substituent is independently selected from the group consisting of alkyl (linear and branched), cycloalkyl, aryl, substituted aryl, heterocyclyl, heteroaryl, alkylcycloalkyl, alkylaryl, alkylheterocyclyl, alkylheteroaryl, halogen, triflurometyl, nitro, amide, ester (—CO$_2$R), —OC(O)R, —OC(O)CF$_3$, —OSO$_2$R, —OSO$_2$CF$_3$) cyano, alkoxy, alkylamino (mono or di), arylamino (mono or di), —SR, an inorganic support or a polymeric moiety.

The phenanthroline based pincer complexes of formula (I) is selected from HCl(CO)Ru(Phen-(tBu)PNN) (3), H(CO)Ru-(Phen-(tBu)PNN) (4) and H(CO)Ru($\eta$1BH4)(Phen-(tBu)PNN) (5a).

The present invention provides a process for the preparation of novel phenanthroline based pincer complexes of formula (I) comprising the steps of:

a) Adding solution of Lithium diisopropylamide and tBuOK in suitable solvent to a solution of 2-methyl-1,10-phenanthroline (1) in ether at temperature in the range of 0 to 5° C. followed by stirring the reaction mixture for the period ranging from 30 to 40 min at the same temperature;

b) Adding a solution of di-tert-butylchlorophosphine in ether with constant stirring for further 1 to 2 hr at temperature in the range of −50 to −78° C. followed by stirring at temperature ranging from 25 to 30° C. for the period in the range of 12 to 14 hrs to obtain Phen-PNN (tBu) (2);

c) Heating the reaction mixture of compound of step (b), RuHCl(CO)(PPh$_3$)$_3$ in THF at temperature in the range of 60 to 70° C. for the period ranging from 5 to 6 hr to afford HCl(CO)Ru(Phen-(tBu)PNN) (3);

d) Adding Sodium bis(trimethylsilyl)amide to a solution of compound of step (c) in C$_6$H$_6$ to obtain phenanthroline based pincer complexes of formula H(CO)Ru-(Phen-(tBu)PNN) (4);

e) Stirring the reaction mixture comprising compound of step (c) and NaBH$_4$ in toluene and ethanol at temperature in the ranging from 50 to 70° C. for the period ranging from 10 to 15 min then at room temperature for the period in the range of 4 to 6 hr to afford H(CO)Ru($\eta^1$BH$_4$)(Phen-(tBu)PNN) (5a).

The solvent in step (a) is selected from hexane heptane, tetrahydrofuran (THF) diethyl ether, toluene and etheylbenzene.

The step (c) is carried out under argon atmosphere.

The 'N arm' in the Milstein catalyst is hemilabile in nature and it can dissociate during the course of catalysis. Thus, under extreme conditions and by use of early transition elements (Fe, Co, Ni etc.,) metal can come out from the ligand core and generates inactive metal particles (data not available). However in the phenanthroline based system the dissociation is restricted and thus gives the unique stability to the metal centre. Py-$^t$BuPNN ligand (liquid state) is highly moisture and air sensitive, due to this complexation has been achieved under extremely inert atmosphere (glovebox), however phenanthroline ligand (solid state) is very much stable and can handled without any special care under an ordinary atmosphere.

The catalyst are stable at normal atmospheric pressure, higher temperatures too [stable up to 180° C. without any decomposition for about 30 min in solid state and stable up to 200° C. for about 1 hr in solution state (2 mL of mesitylene)].

The phenanthroline based pincer complexes have unique metal stability resistant towards oxygen and moisture.

The pincer based phenanthroline catalyst is used to catalyze hydrogenation and dehydrogenation reactions.

Figure 2:
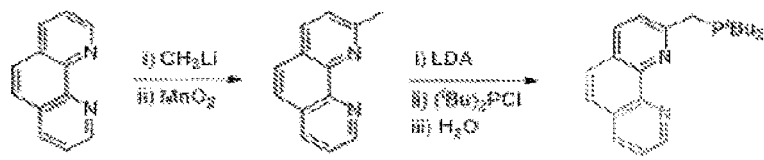
FIG. 2 depicts the schematic representation of synthesis of Phen-$^t$BuPNN
Figure 3:
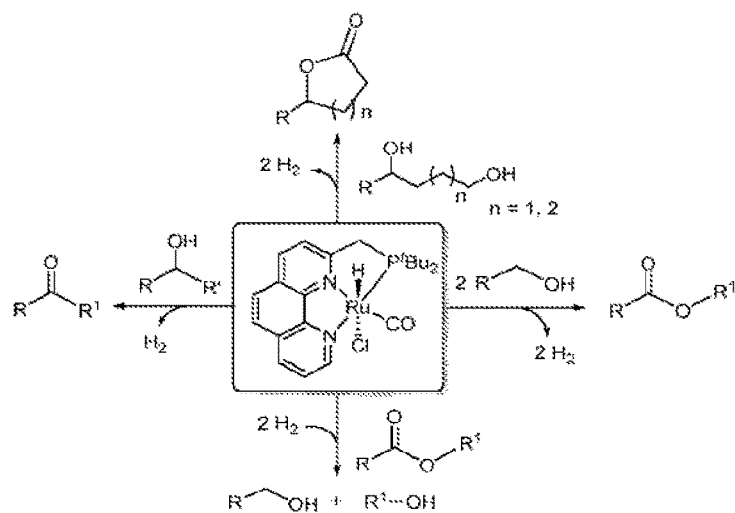
FIG. 3 depicts the schematic representation of hydrogenation of esters to alcohols, lactones to diols, alcohol to esters, diols to lactones and secondary alcohols to ketones.
Figure 4:
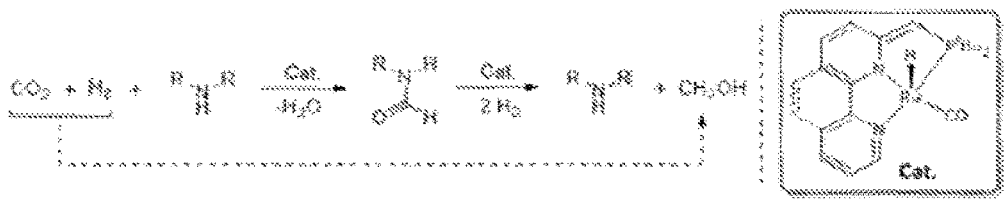
FIG. 4 depicts the schematic representation of process for preparation of methanol from carbon dioxide using catalyst of formula 1 and secondary amine

The pincer based phenanthroline catalyst catalyses reactions selected from, but not limited to hydrogenation of esters to alcohols, lactones to diols, alcohol to esters, diols to lactones and secondary alcohols to ketones, as shown in FIG. 2 and Tables 1-4.

The said catalyst is used for hydrogenation of esters to alcohols as shown in table 1.

TABLE 1

Catalytic hydrogenation of esters to alcohols.

$$R\overset{O}{\underset{\|}{C}}O-R' \xrightarrow[\text{THF, 110° C.}]{\text{Cat.}} R\text{CH}_2\text{OH} + R'\text{—OH}$$

| Entry | Catalyst | esters | products | Yield (%)[b] |
|---|---|---|---|---|
| 1 | 3 | ethyl acetate (CH₃CO₂CH₂CH₃) | H₃C-CH₂-OH | 86 |
| 2[a] | 5a | ethyl acetate (CH₃CO₂CH₂CH₃) | H₃C-CH₂-OH | 92 |
| 3 | 3 | butyl butyrate | butanol | 89 |
| 4 | 3 | ethyl phenylacetate | 2-phenylethanol + H₃C-CH₂-OH | 91 |
| 5 | 3 | ethyl benzoate | benzyl alcohol + H₃C-CH₂-OH | 95 |
| 6 | 3 | ethyl 4-methylbenzoate | 4-methylbenzyl alcohol + H₃C-CH₂-OH | 98 |
| 7 | 3 | ethyl 4-chlorobenzoate | 4-chlorobenzyl alcohol + H₃C-CH₂-OH | 92 |
| 8 | 3 | methyl benzoate | benzyl alcohol + CH₃OH | 94 |
| 9 | 3 | benzyl benzoate | benzyl alcohol | 90 |
| 10 | 5a | HCO₂Me | CH₃OH | 89 |

[a]without ᵗBuOK. [b]yields are based on aromatic alcohols (entries 4-9).

The said catalyst is used for hydrogenation of lactones to diols as shown in table 2.

TABLE 2

Catalytic hydrogenation of lactones to diols.

| Entry | Catalyst | lactones | diols (yield %) |
|---|---|---|---|
| 1 | 3 | γ-butyrolactone | HO-(CH$_2$)$_4$-OH (72) |
| 2 | 5a | γ-butyrolactone | HO-(CH$_2$)$_4$-OH (81) |
| 3 | 5a | δ-valerolactone | HO-(CH$_2$)$_5$-OH (79) |
| 4 | 5a | phthalide | 1,2-benzenedimethanol (68) |

The said catalyst is used for dehydrogenation of alcohols to esters as shown in table 3.

TABLE 3

Catalytic dehydrogenation of alcohols to esters and dihydrogen.

$$2\ R\text{-CH}_2\text{OH} \xrightarrow[\Delta]{\text{Cat.}} R'\text{C(O)O-CH}_2\text{-R} + 2\ H_2 \uparrow$$

| Entry | Catalyst[a] | alcohols | esters (yield %) |
|---|---|---|---|
| 1 | 3 | ethanol | ethyl acetate (59) |
| 2 | 3 | 1-butanol | butyl butyrate (78) |
| 3 | 3 | 1-hexanol | hexyl hexanoate (92) |
| 4 | 3 | benzyl alcohol | benzyl benzoate (97) |
| 5 | 5a | 1-butanol | butyl butyrate (81) |

[a] in case of Cat. 3 one equiv. of $^t$BuOK (w.r.t Cat. 3) was used.

In another preferred embodiment, said catalyst is used for dehydrogenation of diols to lactones as shown in table 4.

TABLE 4

Catalytic dehydrogenation of diols to lactones and dihydrogen.

| Entry | Catalyst | diols | lactones (yield %) |
|---|---|---|---|
| 1 | 3 | HO~~~OH | (72) |
| 2 | 3 | benzene-1,2-diyldimethanol | (78) |
| 3 | 3 | pentane-1,4-diol | (66) |

The said catalyst is used for dehydrogenation of secondary alcohols to ketones as shown table 5.

TABLE 5

Catalytic dehydrogenation of sec. alcohols to ketones.

| Entry | Catalyst | sec. alcohols | ketones (yield %) |
|---|---|---|---|
| 1 | 3 | cyclohexanol | (43) |
| 2 | 3 | 1-phenylethanol | (74) |

TABLE 5-continued

Catalytic dehydrogenation of sec. alcohols to ketones.

| Entry | Catalyst | sec. alcohols | ketones (yield %) |
|---|---|---|---|
| 3 | 5a | 1-phenylethanol | 87 |
| 4 | 3 | 1-(p-tolyl)ethanol | (80) |
| 5 | 3 | 1-(4-fluorophenyl)ethanol | (72) |
| 6 | 3 | 1-(naphthalen-2-yl)ethanol | (76) |

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration and therefore should not be construed to limit the scope of the invention.

Example 1: Synthesis of Phen-PNN($^t$Bu)

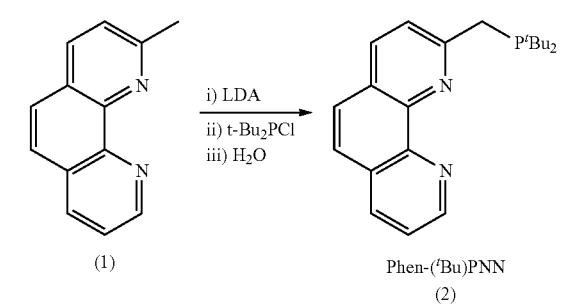

An oven-dried 250 mL two-necked round bottom flask equipped with an argon inlet, a stirring bar and dropping funnel is cooled under a stream of argon. The flask is then charged with 1.94 g (10.0 mmol) of 2-methyl-1,10-phenanthroline (1) in 50 mL dry ether. The solution was cooled to 0° C. and a 1.8 M solution of LDA in heptane/THF/etheylbenzene (6.2 mL, 11.0 mmol) was added via a syringe (15 min) followed by addition of tBuOK (2 mmol). The resulting brown coloured mixture was stirred for 30 min at the same temperature and a solution of di-tert-butylchlorophosphine (1.99 g, 11.0 mmol) in 10 mL dry ether was added dropwise (10 min). Continue the stirring for further 1 hr at −78° C. and the mixture was allowed slowly to warm up to 30° C. and continue the stirring for 12 hrs at the temperature. To this reaction mixture was added 20 mL of degassed water and the ether phase was separated under $N_2$ atmosphere. The aqueous phase was extracted with ether (2×20 mL). The combined ether solutions were dried over anhydrous $Na_2SO_4$, filtered, and the solvent was removed under vacuum to get yellowish-white solid. This was crystallized from mixture of toluene:ether (1:2) at ca. 0° C. to yield 2.27 g (67%) of 2-((di-tert-butylphosphanyl)methyl)-1,10-phenanthroline [Phen-($^t$Bu)PNN] (2) as a white solid.

$^{31}P\{^1H\}$NMR (120 MHz, CDCl$_3$): 38.13. $^1$H NMR (300 MHz, CDCl$_3$): δ 1.19 (d, $J_{PH}$=10.0 Hz, 18H, P(C(CH$_3$)$_3$)$_2$), 3.15 (d, $J_{PH}$=3.0 Hz, 2H, P—CH$_2$), 7.43-7.50 (m, 1H), 7.59-7.64 (m, 1H), 7.73 (d, $J_{HH}$=9.0 Hz, 2H), 8.06 (d, $J_{HH}$=9.0 Hz, 1H), 8.25 (dd, $J_{HH}$=3.0 Hz and $J_{HH}$=9.0 Hz 1H), 9.21 (dd, $J_{HH}$=3.0 Hz and $J_{HH}$=9.0 Hz 1H). $^{13}$C$\{^1$H$\}$ NMR (75 MHz, CDCl$_3$): δ 25.62 (s, P(C(C'H$_3$)$_3$), 25.70 (s, P(C(C"H$_3$)$_3$), 31.25 (d, $J_{PC}$=21.0 Hz, PCH$_2$), 31.56 (d, $J_{PC}$=23.2 Hz, P(C(CH$_3$)$_3$)$_2$), 122.59 (s), 123.53 (s), 125.37 (s), 126.33 (s), 126.33 (s), 128.76 (s), 135.79 (s), 136.00 (s), 145.80 (s), 146.09 (s), 150.16 (s), 159.46 (d, $J_{PC}$=14.0 Hz). HRMS (FAB) Calculated for $C_{21}H_{27}N_2P$ [MH$^+$]: 338.4348. Found: 238.4361.

Example 2: Synthesis of HCl(CO)Ru(Phen-($^t$Bu)PNN) (3)

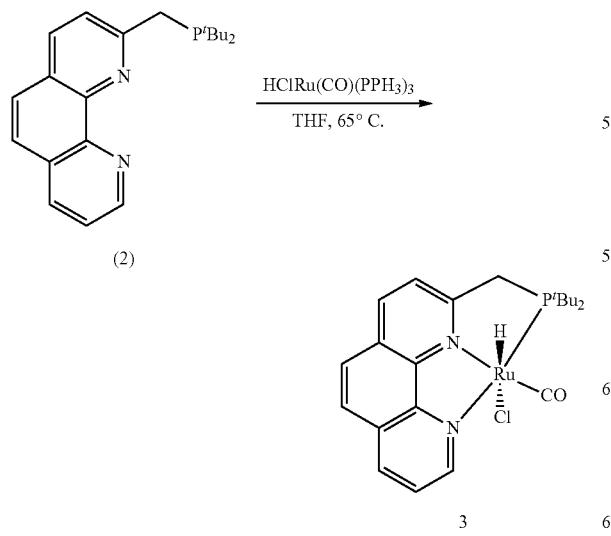

(2)

3

To an oven dried 25 mL pressure vessel equipped with magnetic stirring bar was added Phen-($^t$Bu)PNN (2) (199 mg, 0.52 mmol), RuHCl(CO)(PPh$_3$)$_3$ (476 mg, 0.5 mmol), and 10 mL dry THF under argon atmosphere. The flask was sealed and heated at 65° C. (bath temperature) for 5 hr with constant stirring, then cooled to room temperature to lead to reddish-orange solid. Then the solvent was decanted and the solid thus obtained was washed with diethyl ether (3×3 mL), followed by dried under vacuum to give analytically pure complex 3 (212 mg, 88%).

IR (KBr pellet, cm$^{-1}$): 1995, 1900. $^{31}$P$\{^1$H$\}$NMR (120 MHz, CD$_2$Cl$_2$): 108.21 (s). $^1$H NMR (300 MHz, CD$_2$Cl$_2$): δ −15.30 (d, $J_{PH}$=24.0 Hz, Ru—H), 1.29 (d, $J_{PH}$=15.0 Hz, 9H, P(C(CH$^a_3$)$_3$), 1.58 (d, $J_{PH}$=6.0 Hz, 9H, P(C(CH$^b_3$)$_3$), AB system centered at 3.82 and 3.97 (ABq, $J_{HH}$=18.0 Hz and $J_{PH}$=12.0 Hz, 2H, PCH$^a$H$^b$), 7.78 (dd, 1H, $J_{HH}$=9.0 Hz and $J_{HH}$=7.89 (d, $J_{HH}$=9.0 Hz, 1H), 7.93-7.98 (m, 2H), 8.39 (dd→t, $J_{HH}$=9.0 Hz, 1H), 9.43 (br m, 1H). $^{13}$C$\{^1$H$\}$NMR (75 MHz, CD$_2$Cl$_2$): 28.50 (d, $J_{PC}$=3.0 Hz, P(C(C$^a$H$_3$)$_3$), 29.96 (d, $J_{PC}$=3.0 Hz, P(C(C$^b$H$_3$)$_3$), 36.49 (d, $J_{PC}$=23.0 Hz, PCH$_2$), 37.40 (d, $J_{PC}$=15.0 Hz, P(C$^a$(CH$_3$)$_3$), 37.76 (d, $J_{PC}$=16.5 Hz, P(C$^b$(CH$_3$)$_3$), 122.23 (d, J=8.0 Hz), 125.15 (d, J=2.3 Hz), 126.17 (s), 126.36 (s), 127.78 (s), 130.08 (s), 135.42 (s), 135.86 (s), 153.19 (d, J=1.0 Hz), 161.49 (d, J=5.0 Hz), 208.31 (d, $J_{PC}$=14.8 Hz, Ru—CO). HRMS (FAB) Calculated for $C_{22}H_{28}N_2$OPRu [M-Cl]$^-$: 468.5228. Found: 468.5239.

Example 3: Synthesis of H(CO)Ru$^-$(Phen-($^t$Bu)PNN) (4)

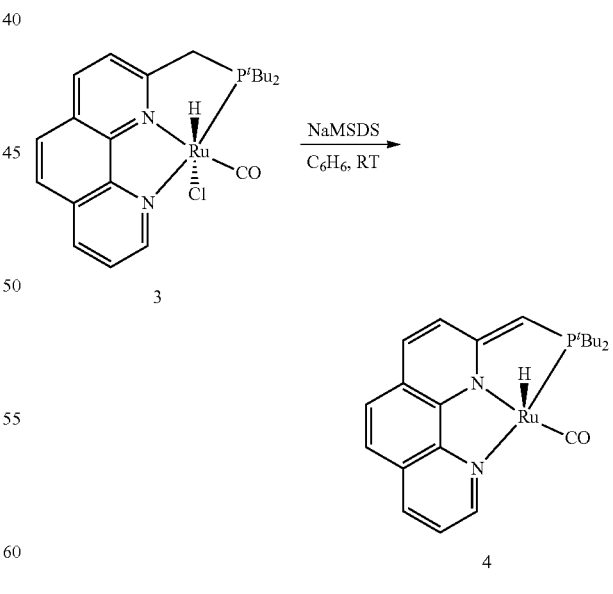

3

4

5.0 mg. of HCl(CO)Ru(Phen-($^t$Bu)PNN) (3) (0.01 mmol) were placed into a J. Young NMR tube, dissolved in ~0.5 mL of C$_6$H$_6$ and 1 eq. of NaHMDS (2.5 mg) was added to generate dark yellowish-brown complex 4. The resulting complex 4 exhibits a broad singlet at 91.53 in $^{31}$P$\{^1$H$\}$NMR.

Example 4: Synthesis of H(CO)Ru(η¹BH₄)(Phen-(ᵗBu)PNN) (5a)

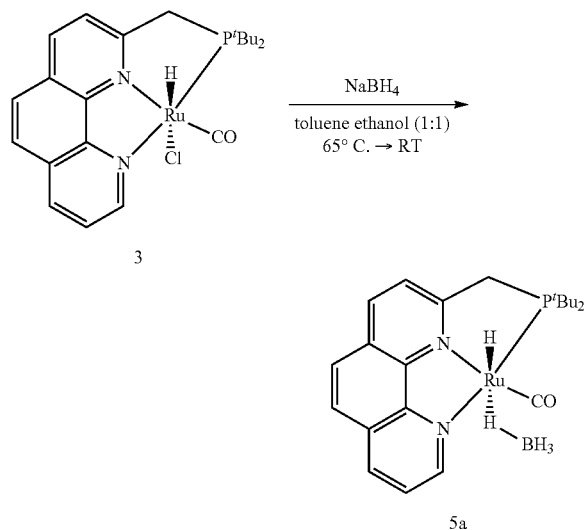

50 mg of HCl(CO)Ru(Phen-(tBu)PNN) (3) (0.1 mmol) and NaBH₄ (19 mg, 0.5 mmol) were placed in a 15 mL Schlenk flask equipped with a Teflon-coated magnetic stirring bar. A 1:1 mixture of toluene and ethanol (2 mL) was added to the flask. It was then stirred at 60° C. for 15 min then at room temperature for 5 hr. Solvent was removed in vacuo and the resulted residue was dissolved in dry $CH_2Cl_2$ (5 mL) and the remaining insoluble materials were removed by filtration through a celite pad. The filtrate was concentrated to ca. 0.3 mL and 3 mL of hexane was added to cause precipitation of a orange-yellow solid, which was filtered, dried under vacuum to give 40 mg (81%) of RuH(CO)(η¹BH₄)Phen-(ᵗBu)PNN (5a).

$^{31}P\{^1H\}$NMR (200 MHz, $CD_2Cl_2$): 113.8 (s). $^1H$ NMR (300 MHz, $CD_2Cl_2$): −12.60 (d, $^2J_{PH}$=22.0 Hz, 1H, Ru—H), −2.28 to −1.86 (br d, 4H, Ru—HBH₃), 1.31 (d, $J_{PH}$=14.0 Hz, 9H, P(C($CH^a_3$)₃)), 1.56 (d, $J_{PH}$=10.5 Hz, 9H, P(C($CH^b_3$)₃)), 3.58-3.72 (m, 2H, PCH$^a$H$^b$), 7.68-7.71 (m, 1H), 7.85 (d, $J_{HH}$=8.0 Hz, 1H), 7.90-7.97 (m, 2H), 8.42 (m, 1H), 9.46-9.49 (br m, 1H).

Example 5: Hydrogenation Process Experimental Details

A 90 mL Fischer-Porter tube was charged under argon with catalyst 3 (0.02 mmol), ᵗBuOK (0.02 mmol), ester (4.0 mmol), and THF (2 mL). The Fischer-Porter tube was purged by three successive cycles of pressurization/venting with H₂ (15 psi), then pressurized with H₂ (150 psi). The solution was heated at 110° C. (bath temperature) with stirring for 16 hr. After cooling to room temperature, the excess H₂ was vented carefully and the products were analyzed by GC-MS and determined by GC using m-xylene as an internal standard.

Example 6: Hydrogenation of Lactones to Diols

A 90 mL Fischer-Porter tube was charged under argon with catalyst (0.02 mmol), ᵗBuOK (0.02 mmol; in case of Cat. 3), ester (4.0 mmol), and THF (2 mL). The Fischer-Porter tube was purged by three successive cycles of pressurization/venting with H₂ (15 psi), then pressurized with H₂ (150 psi). The solution was heated at 110° C. (bath temperature) with stirring for 16 hr. After cooling to room temperature, the excess H₂ was vented carefully and the products were determined by GC using m-xylene as an internal standard.

TABLE 2

Catalytic hydrogenation of lactones to diols.

| Entry | Catalyst | lactones | diols (yield %) |
|---|---|---|---|
| 1 | 3 | γ-butyrolactone | HO-(CH₂)₄-OH (72) |
| 2 | 5a | γ-butyrolactone | HO-(CH₂)₄-OH (81) |
| 3 | 5a | δ-valerolactone | HO-(CH₂)₅-OH (79) |
| 4 | 5a | phthalide | 1,2-benzenedimethanol (68) |

Example 7: Dehydrogenation of Alcohols to Esters

Complex 3 or 5a (0.02 mmol) and primary alcohol (5 mmol) were added to a 15 mL Schlenk flask under an atmosphere of argon. The flask was equipped with a reflux condenser and the neat solution was heated with stirring in an open system under argon for 14 hr (Table 3) at the boiling point of the respective alcohols. The reaction products were analyzed by GC-MS. After cooling to room temperature, m-xylene (1 mmol) was added as internal standard to the reaction mixture and the products were quantitatively analyzed by GC.

TABLE 3

Catalytic dehydrogenation of alcohols to esters and dihydrogen.

$$2 \text{ R}\text{—CH}_2\text{OH} \xrightarrow[\Delta]{\text{Cat.}} \text{R'C(O)OCH}_2\text{R} + 2\text{ H}_2\uparrow$$

| Entry | Catalyst[a] | alcohols | esters (yield %) |
|---|---|---|---|
| 1 | 3 | H₃C-CH₂-OH (ethanol) | ethyl acetate (59) |
| 2 | 3 | 1-butanol | butyl butanoate (78) |
| 3 | 3 | 1-hexanol | hexyl hexanoate (92) |
| 4 | 3 | benzyl alcohol | benzyl benzoate (97) |
| 5 | 5a | 1-butanol | butyl butanoate (81) |

[a] in case of Cat. 3 one equiv of ⁱBuOK (w.r.t Cat. 3) was used.

Example 8: Dehydrogenation of Diols to Lactones

Complex 3 (0.02 mmol), ⁱBuOK (0.02 mmol), diol (2 mmol), and m-xylene (2 mL) were added to a 15 mL Schlenk flask under an atmosphere of argon. The flask was equipped with a reflux condenser and the solution was heated with stirring in an open system under argon at 155° C. (bath temperature). After cooling to room temperature the products were analyzed by GC-MS.

TABLE 4

Catalytic dehydrogenation of diols to lactones and dihydrogen.

$$\text{HOCH}_2\text{-(...)-CH}_2\text{OH} \xrightarrow[\text{m-xylene, 155° C.}]{\text{Cat. + }^t\text{BuOK}} \text{lactone} + 2\text{ H}_2\uparrow$$

| Entry | Catalyst | diols | lactones (yield %) |
|---|---|---|---|
| 1 | 3 | HO-(CH₂)₄-OH | γ-butyrolactone (72) |
| 2 | 3 | 1,2-benzenedimethanol | phthalide (78) |
| 3 | 3 | pentane-1,4-diol | γ-valerolactone (66) |

Example 9: Dehydrogenation of Sec.Alcohols to Ketones and Dihydrogen

Complex 3 or 5a (0.02 mmol), $^t$BuOK (in case of cat. 3; 0.02 mmol), sec.alcohols (2.5 mmol), and m-xylene (2 mL) were added to a 15 mL Schlenk flask under an atmosphere of argon. The flask was equipped with a reflux condenser and the solution was heated with stirring in an open system under argon at 155° C. (bath temperature) for about 24 hr. After cooling to room temperature, the products were analyzed by GC.

TABLE 5

Catalytic dehydrogenation of sec. alcohols to ketones.

| Entry | Catalyst | sec. alcohols | ketones (yield %) |
|---|---|---|---|
| 1 | 3 | cyclohexanol | cyclohexanone (43) |
| 2 | 3 | 1-phenylethanol | acetophenone (74) |
| 3 | 5a | 1-phenylethanol | acetophenone (87) |
| 4 | 3 | 1-(p-tolyl)ethanol | 4′-methylacetophenone (80) |
| 5 | 3 | 1-(4-fluorophenyl)ethanol | 4′-fluoroacetophenone (72) |
| 6 | 3 | 1-(naphthalen-2-yl)ethanol | 2-acetonaphthone (76) |

Example 10: Process for the Synthesis of Methanol from Carbon Dioxide Using Ruthenium (II) Based Pincer-Type Complexes Catalyst The process for the synthesis of methanol from carbon dioxide by using single catalytic system comprising the steps of:
a) mixing catalyst, secondary amine and solvent to obtain a solution;
b) adding potassium tert-butoxide (if applicable) to the solution obtained in step (a) to obtain a solution;
c) pressurizing the solution as obtained in step (b) with carbon dioxide at 10 atmosphere followed by $H_2$ atmosphere in the range of 30-40 atm to obtain a solution;
d) heating the solution as obtained in step (c) in the range of 110° C.-120° C. with stirring for 12-14 hrs to obtain a solution;
e) removing excess gases from the solution as obtained in step (d) to obtain N-formylated product of secondary amine;
f) adding catalyst and potassium tert-butoxide (if applicable)
g) and pressurizing with $H_2$ in the range of 40-45 atmosphere followed by heating the solution in the range of 110-120° C. with stirring for 18-20 hrs to obtain methanol and secondary amine.

The solvent used is tetrahydrofuran, 1,4-dioxane, toluene, mesitylene, xylene etc., The ruthenium (II) based pincer-type complexes catalyst is selected from HCl(CO)Ru(Phen(tBu)PNN), H(CO)Ru-(Phen-(tBu)PNN), HCl(CO)Ru(BPy-tPNN), [H(CO)Ru⁻(BPy-tPNN)], and HCl(CO)Ru(Py-$^t$PNN)].

The said secondary amine may be reused and is selected from:

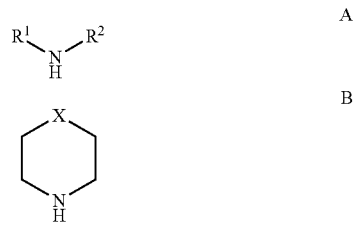

Wherein;
X is selected from the group consisting of NH, $CH_2$ and O $R^1$ and $R^2$ are the same or different and each such substituent is independently selected from the group consisting of alkyl (linear, branched), cyclo (up to 7 membered, which may be further mono, di, tri or tetra substituted and selected from the group consisting of alkyl (linear and branced), aryl (further substituted), cycloalkyl, alkylaryl, alkylheterocyclyl, alkylheteroaryl, halogen, triflurometyl, nitro, alkoxy, dialkylamino, diarylamino, and —SR), cycloalkyl, aryl (which may be further mono, di, tri or tetra substituted), heterocyclyl, heteroaryl, alkylcycloalkyl, alkylaryl, alkylheterocyclyl, and alkylheteroaryl.

The cascade hydrogenation of carbon dioxide to methanol by a single molecular catalyst involves two steps, a) conversion of carbon dioxide to formamide, b) effective formamide hydrogenation to methanol and corresponding amine. The reaction is very selective and operates under mild conditions such as low pressure and temperature without the need of any strong acid.

According to the present invention, the schematic representation of instant process is given in FIG. 1.

Example 11

A 30 mL autoclave equipped with a magnetic stirring was charged under argon with catalyst 3 (0.01 mmol), $^tBuOK$ (0.011 mmol), morpholine (5.0 mmol), and THF (5 mL). The autoclave was pressurized with $CO_2$ (10 atm) followed by $H_2$ (30 atm). The solution was heated at 120° C. (bath temperature) with stirring for 12 hrs. After cooling to 30° C., the excess gases were vented carefully (the obtained product is N-formyl morpholine). Fresh catalyst 3 (0.01 mmol) and $^tBuOK$ (0.011 mmol) were once again added and the autoclave was pressurized with $H_2$ (40 atm). The solution was heated at 120° C. (bath temperature) with stirring for 18 hrs. After cooling to 30° C., the excess $H_2$ was vented carefully and the products (methanol and morpholine) were analysed by GC-MS and determined by GC using m-xylene as an internal standard. The methanol was distilled from the reaction mixture.

Example 12

A 30 mL autoclave equipped with a magnetic stirring was charged under argon with catalyst 3 (0.01 mmol), $^tBuOK$ (0.011 mmol), piperidine (5.0 mmol), and THF (5 mL). The autoclave was pressurized with $CO_2$ (10 atm) followed by $H_2$ (30 atm). The solution was heated at 120° C. (bath temperature) with stirring for 14 hrs. After cooling to 30° C., the excess gases were vented carefully (the obtained product is N-formyl piperidine). Fresh catalyst 3 (0.01 mmol) and $^tBuOK$ (0.011 mmol) were once again added and the autoclave was pressurized with $H_2$ (45 atm). The solution was heated at 120° C. (bath temperature) with stirring for 20 hrs. After cooling to 30° C., the excess $H_2$ was vented carefully and the products (methanol and piperidine) were analysed by GC using m-xylene as an internal standard. The methanol was distilled from the reaction mixture.

Example 13

A 30 mL autoclave equipped with a magnetic stirring was charged under argon with catalyst 4 (0.01 mmol), morpholine (5.0 mmol), and THF (5 mL). The autoclave was pressurized with $CO_2$ (10 atm) followed by $H_2$ (30 atm). The solution was heated at 110° C. (bath temperature) with stirring for 12 hrs. After cooling to 30° C., the excess gases were vented carefully (the obtained product is N-formyl morpholine). Fresh catalyst 4 (0.01 mmol) was once again added and the autoclave was pressurized with $H_2$ (40 atm). The solution was heated at 110° C. (bath temperature) with stirring for 18 hrs. After cooling to 30° C., the excess $H_2$ was vented carefully and the products (methanol and morpholine) were analysed by GC using m-xylene as an internal standard. The methanol was distilled from the reaction mixture.

Example 14

A 30 mL autoclave equipped with a magnetic stirring was charged under argon with catalyst 4 (0.01 mmol), piperidine (5.0 mmol), and THF (5 mL). The autoclave was pressurized with $CO_2$ (10 atm) followed by $H_2$ (30 atm). The solution was heated at 120° C. (bath temperature) with stirring for 14 hrs. After cooling to 30° C., the excess gases were vented carefully (the obtained product is N-formyl piperidine). Fresh catalyst 4 (0.01 mmol) was once again added and the autoclave was pressurized with $H_2$ (40 atm). The solution was heated at 110° C. (bath temperature) with stirring for 18 hrs. After cooling to 30° C., the excess $H_2$ was vented carefully and methanol was distilled from the reaction mixture.

Example 15

A 30 mL autoclave equipped with a magnetic stirring was charged under argon with catalyst 4 (0.01 mmol), pyrrolidine (5.0 mmol), and THF (5 mL). The autoclave was pressurized with $CO_2$ (10 atm) followed by $H_2$ (35 atm). The solution was heated at 110° C. (bath temperature) with stirring for 14 hrs. After cooling to 30° C., the excess gases were vented carefully (the obtained product is N-formyl pyrrolidine). Fresh catalyst 4 (0.01 mmol) was once again added and the autoclave was pressurized with $H_2$ (40 atm). The solution was heated at 110° C. (bath temperature) with stirring for 20 hrs. After cooling to 30° C., the excess $H_2$ was vented carefully and the products (methanol and pyrrolidine) were analysed by GC using m-xylene as an internal standard.

Example 16

A 30 mL autoclave equipped with a magnetic stirring was charged under argon with catalyst 4 (0.01 mmol), morpholine (5.0 mmol), and 1,4-dioxane (5 mL). The autoclave was pressurized with $CO_2$ (10 atm) followed by $H_2$ (30 atm). The solution was heated at 120° C. (bath temperature) with stirring for 12 hrs. After cooling to 30° C., the excess gases were vented carefully (the obtained product is N-formyl morpholine). Fresh catalyst 4 (0.01 mmol) was once again added and the autoclave was pressurized with $H_2$ (40 atm). The solution was heated at 110° C. (bath temperature) with stirring for 18 hrs. After cooling to 30° C., the excess $H_2$ was vented carefully and the products (methanol and morpholine) were analysed by GC using m-xylene as an internal standard.

Example 17

A 30 mL autoclave equipped with a magnetic stirring was charged under argon with catalyst 5 (0.01 mmol), $^tBuOK$ (0.011 mmol), morpholine (5.0 mmol), and THF (5 mL). The autoclave was pressurized with $CO_2$ (10 atm) followed by $H_2$ (30 atm). The solution was heated at 110° C. (bath temperature) with stirring for 12 hrs. After cooling to 30° C., the excess gases were vented carefully (the obtained product is N-formyl morpholine). Fresh catalyst 5 (0.01 mmol) and $^tBuOK$ (0.011 mmol) were once again added and the autoclave was pressurized with $H_2$ (40 atm). The solution was heated at 110° C. (bath temperature) with stirring for 18 hrs. After cooling to 30° C., the excess $H_2$ was vented carefully and methanol was distilled from the reaction mixture.

Example 18

A 30 mL autoclave equipped with a magnetic stirring was charged under argon with catalyst 5 (0.01 mmol), $^tBuOK$ (0.011 mmol), piperidine (5.0 mmol), and THF (5 mL). The autoclave was pressurized with $CO_2$ (10 atm) followed by $H_2$ (40 atm). The solution was heated at 120° C. (bath temperature) with stirring for 14 hrs. After cooling to 30° C., the excess gases were vented carefully (the obtained product is N-formyl piperidine). Fresh catalyst 5 (0.01 mmol) and $^t$BuOK (0.011 mmol) were once again added and the autoclave was pressurized with $H_2$ (40 atm). The solution was heated at 120° C. (bath temperature) with stirring for 20 hrs. After cooling to 30° C., the excess $H_2$ was vented carefully and the products (methanol and piperidine) were analysed by GC using m-xylene as an internal standard.

Example 19

A 30 mL autoclave equipped with a magnetic stirring was charged under argon with catalyst 6 (0.01 mmol), morpholine (5.0 mmol), and THF (5 mL). The autoclave was pressurized with $CO_2$ (10 atm) followed by $H_2$ (30 atm). The solution was heated at 110° C. (bath temperature) with stirring for 14 hrs. After cooling to 30° C., the excess gases were vented carefully (the obtained product is N-formyl morpholine). Fresh catalyst 6 (0.01 mmol) was once again added and the autoclave was pressurized with $H_2$ (45 atm). The solution was heated at 110° C. (bath temperature) with stirring for 20 hrs. After cooling to 30° C., the excess $H_2$ was vented carefully and the products were analysed by GC.

Example 20

A 30 mL autoclave equipped with a magnetic stirring was charged under argon with catalyst 6 (0.01 mmol), piperidine (5.0 mmol), and THF (5 mL). The autoclave was pressurized with $CO_2$ (10 atm) followed by $H_2$ (40 atm). The solution was heated at 110° C. (bath temperature) with stirring for 12 hrs. After cooling to 30° C., the excess gases were vented carefully (the obtained product is N-formyl piperidine). Fresh catalyst 6 (0.01 mmol) was once again added and the autoclave was pressurized with $H_2$ (45 atm). The solution was heated at 110° C. (bath temperature) with stirring for 20 hrs. After cooling to 30° C., the excess $H_2$ was vented carefully and methanol was distilled from the reaction mixture.

Example 21

A 30 mL autoclave equipped with a magnetic stirring was charged under argon with catalyst 7 (0.01 mmol), $^t$BuOK (0.011 mmol), morpholine (5.0 mmol), and THF (5 mL). The autoclave was pressurized with $CO_2$ (10 atm) followed by $H_2$ (40 atm). The solution was heated at 120° C. (bath temperature) with stirring for 14 hrs. After cooling to 30° C., the excess gases were vented carefully (the obtained product is N-formyl morpholine). Fresh catalyst 7 (0.01 mmol) and $^t$BuOK (0.011 mmol) were once again added and the autoclave was pressurized with $H_2$ (45 atm). The solution was heated at 120° C. (bath temperature) with stirring for 20 hrs. After cooling to 30° C., the excess $H_2$ was vented carefully and the products (methanol and morpholine) were analysed by GC using m-xylene as an internal standard.

Example 22

A 30 mL autoclave equipped with a magnetic stirring was charged under argon with catalyst 7 (0.01 mmol), $^t$BuOK (0.011 mmol), piperidine (5.0 mmol), and THF (5 mL). The autoclave was pressurized with $CO_2$ (10 atm) followed by $H_2$ (40 atm). The solution was heated at 120° C. (bath temperature) with stirring for 14 hrs. After cooling to 30° C., the excess gases were vented carefully (the obtained product is N-formyl piperidine). Fresh catalyst 7 (0.01 mmol) and $^t$BuOK (0.011 mmol) were once again added and the autoclave was pressurized with $H_2$ (45 atm). The solution was heated at 120° C. (bath temperature) with stirring for 20 hrs. After cooling to 30° C., the excess $H_2$ was vented carefully and the products (methanol and piperidine) were analysed by GC.

The pincer catalysts used for the hydrogenation of $CO_2$ to MeOH are shown in FIG. 1.

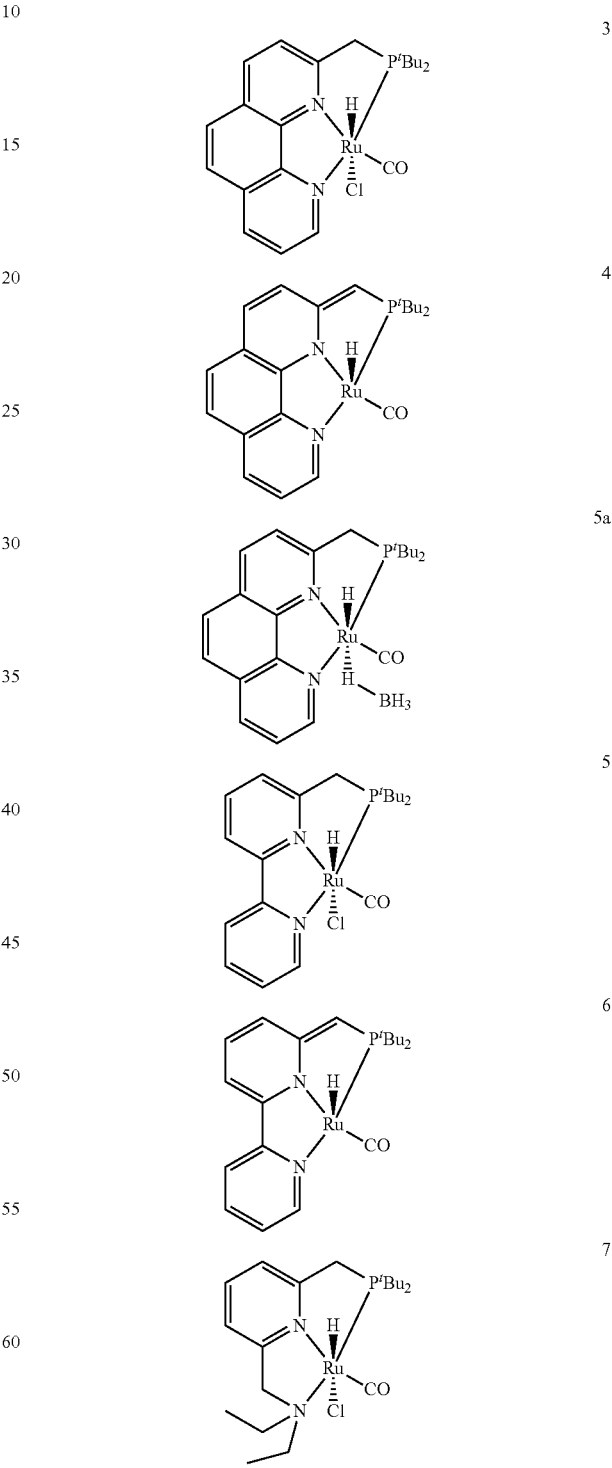

FIG. 1. Pincer catalysts used for the hydrogenation of $CO_2$ to MeOH

The result of catalytic hydrogenation of $CO_2$ to methanol is summarized in table 1:

TABLE 6

Catalytic hydrogenation of CO₂ to MeOH.

| | | 1st stage | | | 2nd stage | | |
|---|---|---|---|---|---|---|---|
| Entry | Catalyst | Amine | Formamide | Yield (%) | Formamide | Products | Yield (%) of methanol |
| 1 | 3 + tBuOK | piperidine | N-formylpiperidine | quantitative | N-formylpiperidine | piperidine + MeOH | 91 |
| 2 | 5 + tBuOK | piperidine | N-formylpiperidine | 93 | N-formylpiperidine | piperidine + MeOH | 84 |
| 3 | 3 + tBuOK | morpholine | N-formylmorpholine | quantitative | N-formylmorpholine | morpholine + MeOH | 93 |
| 4 | 5 + tBuOK | morpholine | N-formylmorpholine | 95 | N-formylmorpholine | morpholine + MeOH | 88 |
| 5 | 6 | morpholine | N-formylmorpholine | 96 | N-formylmorpholine | morpholine + MeOH | 88 |
| 6 | 7 + tBuOK | morpholine | N-formylmorpholine | 62 | N-formylmorpholine | morpholine + MeOH | 35 |
| 7 | 4 | morpholine | N-formylmorpholine | quantitative | N-formylmorpholine | morpholine + MeOH | 97 |
| 8 | 4 (in 1,4-dioxane) | morpholine | N-formylmorpholine | 96 | N-formylmorpholine | morpholine + MeOH | 89 |

TABLE 6-continued

Catalytic hydrogenation of CO₂ to MeOH.

| | | 1st stage | | | 2nd stage | | |
|---|---|---|---|---|---|---|---|
| Entry | Catalyst | Amine | Formamide | Yield (%) | Formamide | Products | Yield (%) of methanol |
| 9 | 4 | piperidine | N-formylpiperidine | 99 | N-formylpiperidine | piperidine + MeOH | 90 |
| 10 | 4 | pyrrolidine | N-formylpyrrolidine | 94 | N-formylpyrrolidine | pyrrolidine + MeOH | 81 |
| 11 | 6 | piperidine | N-formylpiperidine | 81 | N-formylpiperidine | piperidine + MeOH | 42 |
| 12 | 7 + $^t$BuOK | piperidine | N-formylpiperidine | 50 | N-formylpiperidine | piperidine + MeOH | 28 |

Advantages of the Invention

1. Environmentally benign conditions
2. Operationally simple synthetic process
3. solvent-free reaction conditions
4. Direct conversion of alcohols to esters with liberation of hydrogen gas
5. Efficient hydrogenation of esters including lactones to the corresponding alcohols
6. One-pot process catalyzed by a single-site molecularly defined Ru-catalyst
7. Operationally simple synthetic process (low temperature and pressure)
8. Amine acts as auto-catalyst and can be reused
9. Improved yield

The invention claimed is:

1. A phenanthroline pincer complex, wherein said complex is selected from HCl(CO)Ru(Phen-(tBu)PNN) (3), H(CO)Ru-(Phen-(tBu)PNN) (4) and H(CO)Ru(η1BH4)(Phen-(tBu)PNN) (5).

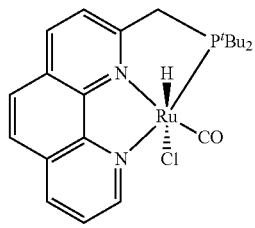

(3)

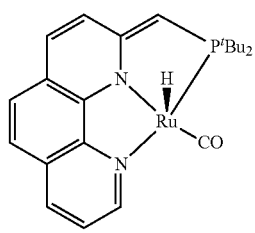

(4)

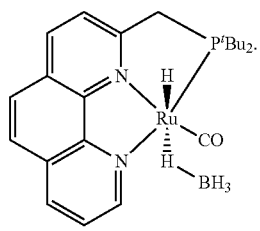
(5a)

2. The phenanthroline pincer complex as claimed in claim 1, wherein said complex is used as a catalyst for hydrogenation of lactones to diols and esters to alcohols.

3. The phenanthroline pincer complex as claimed in claim 2, wherein said catalyst is used for dehydrogenation of diols to lactones, alcohol to esters and secondary alcohols to ketones.

4. A process for the preparation of a phenanthroline pincer complex comprising the steps of:
   a) adding solution of Lithium diisopropylamide and tBuOK in suitable solvent to a solution of 2-methyl-1,10-phenanthroline (1) in ether at a temperature in a range of 0° to 5° C. followed by stirring the reaction mixture for a period in a range of 30 to 40 minutes to obtain a solution;

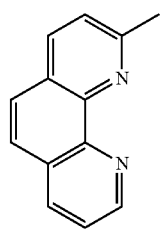
(1)

b) adding a solution of di-tert-butylchlorophosphine in ether to the solution as obtained in step (a) and stirring for a period of 1 to 2 hours at a temperature in a range of −50° C. to −78° C. followed by stirring at temperature in a range of 25° C. to 30° C. for the period in a range of 12 to 14 hours to obtain Phen-PNN-(tBu) (2);

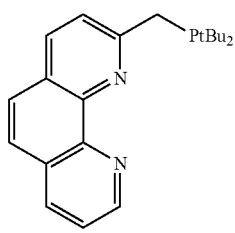
(2)

c) mixing the Phen-PNN(tBu) (2) as obtained in step (b), RuHCl(CO)(PPh$_3$)$_3$ and tetrahydrofuran heating at a temperature in a range of 60° C. to 70° C. for the period in a range of 5 to 6 hours under argon atmosphere to obtain HCl(CO)Ru(Phen-(tBu)PNN) (3);

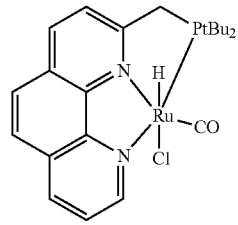
(3)

d) adding Sodium bis(trimethylsilyl)amide to the compound of step (c) in C$_6$H$_6$ to obtain H(CO)Ru-(Phen-(tBu)PNN) (4);

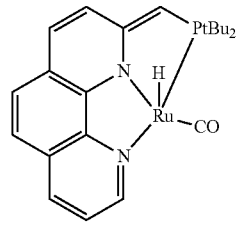
(4)

e) stirring the reaction mixture comprising HCl(CO)Ru(Phen-(tBu)PNN) (3) and NaBH$_4$ in toluene and ethanol at a temperature in a range of 50° C. to 70° C. for a period in a range of 10 to 15 minutes followed by stirring at a temperature in a range of 25° C. to 30° C. for a period in a range of 4 to 6 hours to obtain H(CO)Ru(η1BH4)(Phen-(tBu)PNN) (5).

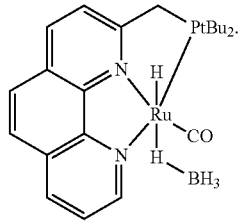
(5)

5. The process as claimed in claim 4, wherein the solvent used in step (a) is selected from hexane, heptane, tetrahydrofuran (THF), diethyl ether, toluene, and etheylbenzene.

* * * * *